United States Patent [19]
Reiss et al.

[11] Patent Number: 5,743,895
[45] Date of Patent: Apr. 28, 1998

[54] DISPOSABLE DIAPER AND METHOD THEREFOR

[75] Inventors: Edward Reiss; Brenda J. Schenk, both of Westport, Conn.

[73] Assignee: RMED International, Inc., Westport, Conn.

[21] Appl. No.: 592,108

[22] Filed: Jan. 26, 1996

[51] Int. Cl.⁶ .............................. A61F 13/15; A61F 13/20
[52] U.S. Cl. .......................... 604/377; 604/367; 604/378
[58] Field of Search .................................... 604/358, 367, 604/370, 377, 378

[56] References Cited

U.S. PATENT DOCUMENTS

| | | | |
|---|---|---|---|
| 3,777,758 | 12/1973 | Mesek et al. | 604/377 |
| 3,945,386 | 3/1976 | Anczurowski et al. | 604/370 |
| 4,324,247 | 4/1982 | Aziz | 604/377 |
| 4,333,463 | 6/1982 | Holtman | 604/378 |
| 5,603,707 | 2/1997 | Trombetta et al. | 604/370 |

FOREIGN PATENT DOCUMENTS

| 1081620 | 8/1967 | United Kingdom | 604/377 |
|---|---|---|---|

*Primary Examiner*—P. Zuttarelli
*Attorney, Agent, or Firm*—Harry M. Weiss; Jeffrey D. Moy; Harry M. Weiss & Associates, P.C.

[57] ABSTRACT

The present invention is directed to an improved disposable diaper and method therefor. The disposable diaper achieves significant fluid absorbency through a wadding batt layer consisting solely of a combination of wood pulp and cotton pulp, rather than through a wadding batt layer comprising wood pulp and a superabsorbent polymer. In this fashion, the disposable diaper minimizes skin irritation that may be caused during rewetting when body waste fluids contacting the superabsorbent polymers carry a portion thereof back out through the diapers into contact with the skins of babies or children using the diapers. The disposable diaper also minimizes skin irritation caused when both the exterior portion of a diaper contacts a child's skin or the skin of a person touching the diaper, by the use of an outer and inner surface layer of a soft, cloth-like, non-woven bond material such as polyester.

13 Claims, 1 Drawing Sheet

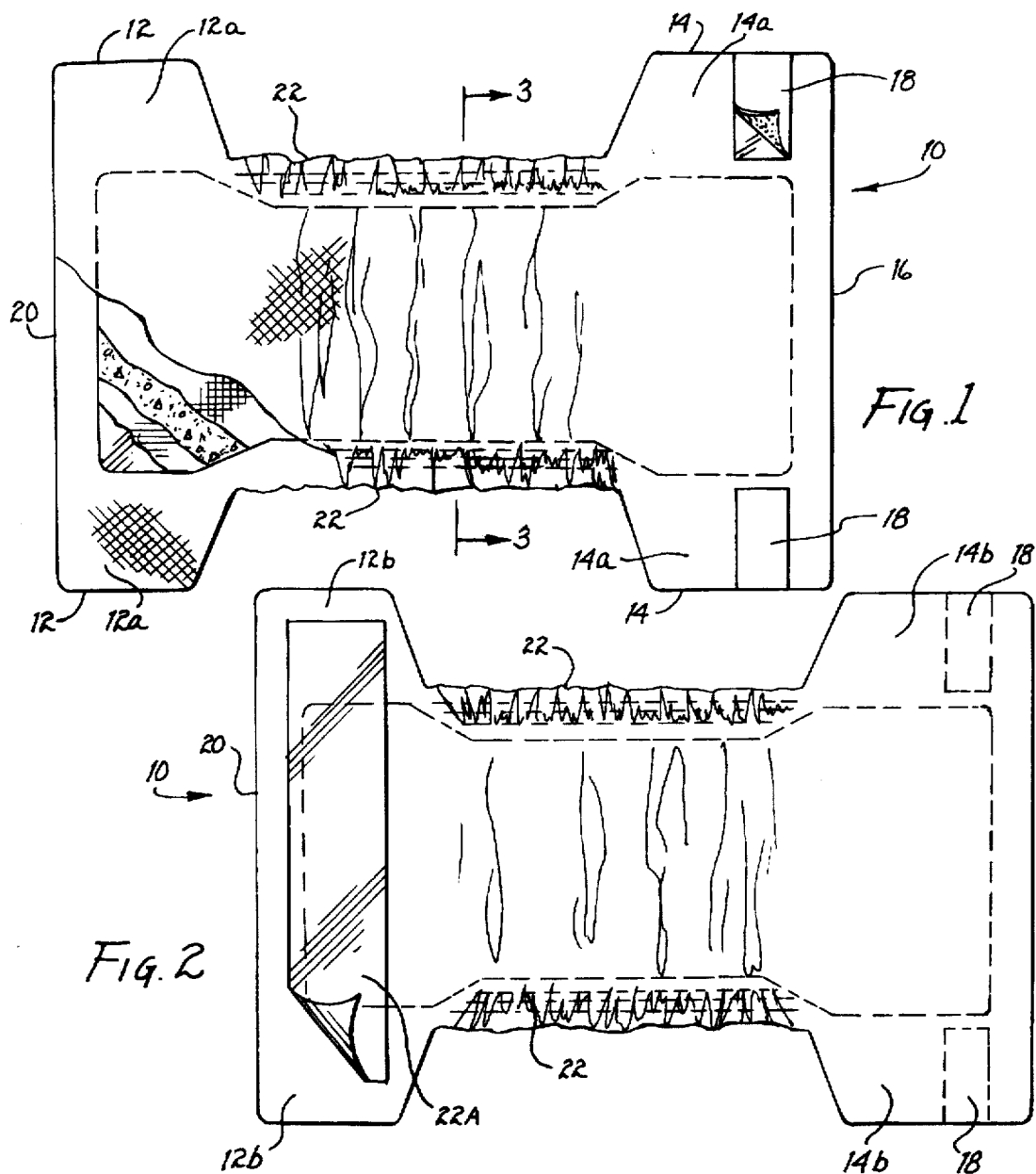
Fig. 1
Fig. 2
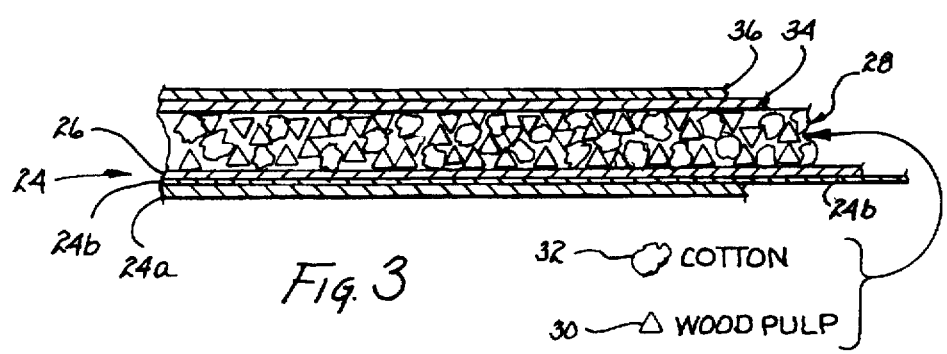
Fig. 3

5,743,895

DISPOSABLE DIAPER AND METHOD THEREFOR

BACKGROUND OF THE INVENTION

1. Field of Invention

This invention relates generally to diapers and methods therefor and, more particularly, to a disposable diaper and method that permits the diaper to achieve fluid absorbency for the comfort of a baby through use of a unique combination of only cotton and wood pulp rather than through the use of chemical additives used by other diaper manufacturers that may irritate a child's skin, and also provides a cloth-like exterior surface on both sides of the diaper that significantly reduces irritation to the portions of a child's, baby's, or adult's skin coming in contact with the outer or inner surfaces of the diaper.

2. Background of the Invention

Disposable diapers are well known and widely used and, over the years, have become the dominant diaper, largely replacing the old form of reusable diaper. Typical disposable diapers generally use an absorbent interior area for absorbing a child's urine, bounded by a thin plastic exterior layer. The interior portion of the typical disposable diaper presently on the market is generally comprised of a bottom layer of non-woven material that is in direct contact with the area of the child's skin covered by the diaper, a backing layer of tissue paper that contacts the bottom portion of the layer of non-woven material, a wadding batt layer of wood pulp that is located between the thin plastic exterior layer and the layer of tissue paper, and, in order to increase the diaper's fluid absorbency, diaper manufacturers add a superabsorbent polymer or other chemical additive to the wadding batt layer. Without the superabsorbent polymer, wood pulp generally absorbs in the range of 12 to 15 times its weight. With the superabsorbent polymer, the wadding batt layer is able to absorb in the range of 30 to 55 times its weight.

The increase in fluid absorbency achieved by adding a superabsorbent polymer to the wadding batt layer comes with a price. Diapers with this polymer additive experience what is known in the industry as "rewet"—i.e., the transfer of wetness from the diaper back to the surface of the diaper and to the child's skin. During this transfer process, some amount of the superabsorbent polymer, which is deposited or formed in the wadding batt layer during manufacture and especially in the areas most likely to become wet or soiled, is transmitted back to the child's skin along with a portion of the fluid that has been initially absorbed by the diaper. The skin of some children is very sensitive and/or allergic to this polymer additive and thus becomes irritated when contacted with the superabsorbent polymer. An amount of the superabsorbent polymer can also come into contact with the skin of a person changing a wet or soiled diaper, and may cause irritation to that person's skin.

The exterior plastic surface portion layer of a typical disposable diaper can also cause irritation to a child's skin contacting this plastic surface layer. This outer plastic layer or covering is relatively abrasive and is a source of irritation to a baby's sensitive skin that contacts this exterior plastic layer during wear. Such contact very often occurs when a portion of the child's body (i.e., any arm, leg, etc.) brushes against the exterior of the diaper during wear, and particularly occurs in the inner thigh area, where the exterior portion of the diaper covering the crotch area is located, when the child's legs are brought close enough together so that the inner thighs come into contact with the portion of the diaper covering the child's crotch area. Contact between the child's skin and the relatively abrasive plastic outer surface of the diaper can be irritating to the child's skin. Such contact can also be irritating to the skin of a person repeatedly handling diapers for purposes of changing the diaper of a baby or child.

Therefore, a need existed to provide an improved disposable diaper and method that increases the fluid absorbency of the wadding batt layer with more natural-type materials and without liquid absorbing chemicals so as to avoid irritation to the skin of certain children during rewetting and/or a person changing the diaper. The improved disposable diaper and method must also have both a soft bottom and top exterior surface portion so as to significantly reduce irritation to the skin of certain children when the inner thigh or other portions of the baby's or child's skin contacts the exterior portion of the disposable diaper during wear. Thus, a baby using such an improved disposable diaper will be very comfortable because of having a high quality, more natural fluid absorbency material that avoids irritations to the skin during rewetting while simultaneously providing soft bottom and top exterior surface portions that avoid irritation to a baby's skin coming in contact with either the top or bottom surface of this improved diaper.

SUMMARY OF THE INVENTION

In accordance with one embodiment of the present invention, it is an object of the present invention to provide an improved disposable diaper and method therefor.

It is another object of the present invention to provide an improved disposable diaper and method that increases the fluid absorbency of the wadding batt layer with the use of a natural material rather than through the addition of a superabsorbent polymer or other form of chemical so as to reduce irritation to the skin of certain children during rewetting.

It is a further object of the present invention to provide an improved disposable diaper and method having soft, cloth-like exterior bottom and top surface portions, so as to reduce irritation to the skin of certain children from contact between the skin and the exterior portions of the diaper during wear.

It is a still further object of the present invention to provide a very comfortable improved disposable diaper and method which both, in combination, increases the fluid absorbency of the wadding batt layer with the use of a natural material rather than through the addition of a superabsorbent polymer or other form of chemical so as to reduce irritation to the skin of certain children during rewetting and also has soft, cloth-like exterior bottom and top surface portions, so as to reduce irritation to the skin of certain children from contact between the skin and the exterior surface portions of the diaper during wear.

BRIEF DESCRIPTION OF THE PREFERRED EMBODIMENTS

In accordance with one embodiment of the present invention, an improved disposable diaper is disclosed. The disposable diaper comprising, in combination: a multi-layered diaper assembly comprising: a first top surface layer comprising a non-woven material upper surface layer and an underlying thin plastic sheet, the non-woven material surface layer being in bonded contact with the thin plastic sheet on a top surface portion thereof; a second layer consisting solely of a mixture of wood pulp and cotton located below a bottom surface portion of the underlying thin plastic sheet; a third layer comprising a thin layer of tissue paper having a top surface portion in contact with a bottom surface portion of the second layer; and a fourth bottom surface layer in contact with a bottom surface portion of the third layer and comprising a non-woven material. The second layer preferably consists solely of from about 20% to about 40% percent cotton pulp and from about 80% to about 60% wood pulp.

In accordance with another embodiment of the present invention, a method for providing a disposable diaper is disclosed. The method comprises the steps of: providing a multi-layered diaper assembly comprising: forming a first top surface layer comprising a non-woven material upper surface layer and an underlying thin plastic sheet, the non-woven material surface layer being in bonded contact with the thin plastic sheet on a top surface portion thereof; forming a second layer consisting solely of a mixture of wood pulp and cotton below a bottom surface portion of the thin plastic sheet; providing a third layer comprising a thin layer of tissue paper having a top surface portion in contact with a bottom surface portion of the second layer; and providing a fourth bottom surface layer in contact with a bottom surface portion of the third layer and comprising a non-woven material. The step of forming the second layer further comprises the step of forming the second layer with from about 20% to about 40% percent cotton pulp and from about 80% to about 60% wood pulp.

The foregoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 1 is an elevated front side view of the disposable diaper of the present invention.

FIG. 2 is an elevated rear side or backside view of the disposable diaper of the present invention.

FIG. 3 is a cross-sectional view of the disposable diaper of FIG. 1 taken along line 3—3 of FIG. 1.

DETAILED DESCRIPTION OF THE PREFERRED EMBODIMENTS

Referring to the embodiment of FIGS. 1 and 2, reference number 10 refers generally to the disposable diaper of this invention. Referring to FIG. 1, a front or interior view of the disposable diaper 10 is shown, in the open position. The disposable diaper 10, like other disposable diapers, comprises front flaps 12 and back flaps 14. Reference numbers 12a and 14a refer to the side portions of the front flaps 12 and the back flaps 14, respectively, that are visible in the front view of the disposable diaper 10 depicted in FIG. 1. Adhered to the back flaps 14a, and oriented substantially parallel to an upper edge 16 of the diaper 10, are preferably two tape assemblies 18. Each tape assembly 18 comprises a base portion that is attached directly to the surface of the diaper 10, and a partially separable adhesive portion that may be peeled from the base portion for adhesion attachment to the reverse side of front flaps 12 (see both FIGS. 1 and 2) when the diaper 10 is being placed on a baby or child. On both sides of the diaper 10, oriented in a substantially perpendicular direction to the upper edge 16 and the lower edge 20, are two elastic portions 22. The elastic portions 22 snugly grip the legs of the child during the wearing of the diaper 10 to, among other things, minimize the leaking of fluid out of the diaper 10.

Referring to FIG. 2, a rear or backside exterior view of the disposable diaper 10 is shown, in the open position. Reference numbers 12b and 14b refer to the sides of the front flaps 12 and the back flaps 14, respectively, that are visible in the rear or backside view of the disposable diaper 10. Adhered to the back flaps 14b, and oriented substantially parallel to the upper edge 16 of the diaper 10, are portions of the two tape assemblies 18. These are continuations of the portions of the tape assemblies 18 which are located on the back flaps 14a, as shown in FIG. 1. Located between tabs 12b is a preferably rectangular plastic strip 22A, which strip 22A receives the adhesive portion of the tape assemblies 18 when the diaper is being placed on a baby or child.

Referring to FIG. 3, a cross-sectional view of the disposable diaper 10 is shown, showing the layers of material comprising the diaper 10. Starting from the exterior of the diaper 10 and moving inward (or going from the top surface of the diaper 10 to the bottom surface of the diaper 10), there is a first layer 24 which comprises a non-woven material upper or outer surface layer 24a and an underlying thin plastic sheet 24b, with the surface layer 24a and the plastic sheet 24b being in bonded contact with each other, preferably in the form of a laminate. Preferably, the thickness of the surface layer 24a is in the range of 1.5 mils, and the thickness of the plastic sheet 24b is in the range of 0.5 mils. In the preferred embodiment, the upper or outer surface layer 24a comprises a non-woven polyester type of material. In contact with the bottom surface of the plastic sheet 24b is, if desired, a thin layer 26, comprising tissue paper. It is possible using certain advanced manufacturing equipment to construct the diaper 10 of this invention without the layer 26 of tissue paper.

In contact with a bottom or inner portion of the tissue layer 26 or, if desired, directly in contact with a bottom or inner surface portion of the plastic sheet 24b, is a second layer 28, which is a wadding batt layer consisting solely of a mixture of wood pulp and cotton pulp. This is illustrated by the symbols 30 depicting wood pulp particles, and the symbols 32 depicting cotton pulp particles. The mixing of cotton pulp and wood pulp creates a blend that is substantially more absorbent than a wadding batt layer comprised entirely of wood pulp. In this regard, wood pulp generally absorbs in the range of 12 to 15 times its weight. Cotton pulp, in contrast, generally absorbs approximately 25 times its weight, depending on the quality of the particular cotton. By mixing cotton pulp with wood pulp in appropriate amounts, the absorbency of the resulting mixture is greater than that of pure wood pulp. In the preferred embodiment of this invention, the second layer 28 is about five-eighths of an inch thick. However, it should be understood that changes can be made in the thicknesses of any of the layers comprising the diaper 10 without departing from the spirit or scope of this invention.

In the preferred embodiment of this invention, wood pulp and cotton pulp are mixed or ground together during the manufacturing process in a two to one ratio using, for example, two strips of wood pulp to one strip of cotton pulp fed into a grinder to create the second layer 28. Thus, the second layer 28 comprises two-thirds wood pulp and one third cotton pulp. Applicants' analysis suggests that a mixture comprising a lower percentage of cotton pulp (perhaps about 20% cotton pulp) and a higher percentage of wood pulp (perhaps about 80%) would also yield significant fluid absorbency benefits. Moreover, Applicants' analysis further suggests that a higher percentage of cotton pulp (perhaps up to about 40% cotton pulp) and a lower percentage of wood pulp (perhaps up to about 60% wood pulp), would yield even greater absorbency than the outer limits noted above, namely, 20% cotton pulp and 80% wood pulp. However, Applicants' analysis suggests that any additional fluid absorbency benefits attributable to the addition of an amount of cotton pulp over the 33.33% mark are relatively marginal, and that such benefits appear to more or less flatten out at the 40% level. Thus, the marginal increase in fluid absorbency coupled with the substantially higher cost of cotton pulp versus wood pulp appears to suggest that the preferred percentage or amount of cotton pulp to be used with wood pulp is about 33.33% (the remaining wood pulp in the mixture is about 66.67%). There is also a manufacturing efficiency that is achieved by maintaining a 2 to 1 ratio of wood pulp and cotton pulp. With these ratios, the second layer 28 can be manufactured using one roll or lap of cotton pulp (not shown) and two rolls or laps of wood pulp (not shown), preferably in one-eighth inch sheets. These sheets or strips can be fed into a hammermill (not shown), which mixes the wood pulp and cotton pulp together in a 2 to 1 ratio. By departing from this ratio, it becomes necessary to either add additional rolls or to vary the thickness of one or more of the strips or to add an additional manufacturing step or steps to create the proper blend.

In contact with a bottom or upper portion of second layer 28 is a third layer 34, comprising tissue paper. Finally, in contact with a bottom or upper portion of third layer 34 is a fourth layer 36, comprising a non-woven bond material such as a polyester type of material. Accordingly, the fourth layer 36 is made of a soft cloth-like type material that is substantially porous, permitting a child's or baby's fluid waste to penetrate therethrough for fluid absorption by the second layer 28 consisting solely of the mixture of cotton pulp and wood pulp, whereas the first layer 24 provides both a barrier layer to prevent fluid from penetrating outwardly therethrough from the second fluid absorbing layer 28 and a soft, cloth-like surface layer (24a) to provide a soft exterior layer that is non-abrasive to the skin of a baby or child or a person diapering the baby or child. Thus, both inner and outer soft layers are provided by this invention.

While the invention has been particularly shown and described with reference to preferred embodiments thereof, it will be understood by those skilled in the art that the foregoing and other changes in form and details may be made therein without departing from the spirit and scope of the invention.

We claim:

1. A disposable diaper comprising, in combinations:
 a multi-layered diaper assembly comprising:
  a first top surface exterior layer assembly comprising a non-woven material having a planar, soft, cloth-like surface layer and an underlying thin, liquid impermeable plastic sheet, said non-woven material surface layer being in bonded contact with said thin plastic sheet on a top surface portion thereof;
  a second layer consisting solely of a blended mixture of wood pulp and cotton pulp having a substantially higher liquid urine absorption than wood pulp and located below a bottom surface of said underlying thin plastic sheet;
  a third layer comprising a thin, planar layer of tissue paper having a top surface portion in contact with a bottom surface portion of said second layer; and
  a fourth bottom surface interior layer in contact with a bottom surface portion of said third layer and comprising a non-woven liquid permeable material having a planar, soft, cloth-like body contact surface portion.

2. A disposable diaper in accordance with claim 1 wherein said second layer consists from about 20% to about 40% percent cotton pulp and from about 80% to about 60% wood pulp.

3. A disposable diaper in accordance with claim 1 wherein said second layer consists from about 25% to about 35% percent cotton pulp and from about 75% to about 65% wood pulp.

4. A disposable diaper in accordance with claim 1 wherein said second layer consists about 33.33% percent cotton pulp and about 66.67% wood pulp.

5. A disposable diaper in accordance with claim 1 wherein said multi-layered diaper assembly further comprises a layer of tissue paper having a top surface thereof in contact with a bottom surface of said underlying thin plastic sheet and a bottom surface thereof in contact with a top surface of said second layer.

6. A disposable diaper in accordance with claim 1 wherein said first layer is about 2 mils thick and said second layer is about five-eighths of an inch thick.

7. A method for providing a disposable diaper comprising the following steps:
 providing a multi-layered diaper assembly comprising:
  forming a first top surface exterior layer assembly comprising a non-woven material having a planar, soft, cloth-like surface layer and an underlying thin liquid impermeable plastic sheet, said non-woven material surface layer being in bonded contact with said thin plastic sheet on a top surface portion thereof,
  forming a second layer consisting solely of a blended mixture of wood pulp and cotton pulp having a substantially higher liquid urine absorption than wood pulp below a bottom surface of said thin plastic sheet;
  providing a third layer comprising a thin planar layer of tissue paper having a top surface portion in contact with a bottom surface portion of said second layer; and
  providing a fourth bottom surface interior layer in contact with a bottom surface portion of said third layer and comprising a non-woven liquid permeable material having a planar, soft, cloth-like, body contact surface portion.

8. The method of claim 7 wherein said second layer comprising from about 20% to about 40% percent cotton pulp and from about 80% to about 60% wood pulp.

9. The method of claim 7 wherein said second layer consists from about 25% to about 35% percent cotton pulp and from about 75% to about 65% wood pulp.

10. The method of claim 7 wherein said second layer consists about 33.33% percent cotton pulp and about 66.67% wood pulp.

11. The method of claim 7 wherein said step of forming said second layer further comprises the step of mixing together separate sources of cotton pulp and wood pulp material.

12. The method of claim 7 further comprising the step of placing a layer comprising tissue paper having a top surface thereof in contact with a bottom surface of said underlying thin plastic sheet and a bottom surface thereof in contact with a top surface of said second layer.

13. The method of claim 7 further comprising the steps of forming said first layer having a thickness of about 2 mils and said second layer having a thickness of about five-eights of an inch.

* * * * *